United States Patent [19]

Bakshi et al.

[11] Patent Number: 4,595,777

[45] Date of Patent: Jun. 17, 1986

[54] SILAHYDROCARBONS FROM ALKYLCHLOROSILANES

[75] Inventors: Kiran R. Bakshi, Murrysville; Anatoli Onopchenko, Monroeville; Edward T. Sabourin, Allison Park, all of Pa.

[73] Assignee: Gulf Research & Development Company, Pittsburgh, Pa.

[21] Appl. No.: 707,881

[22] Filed: Mar. 4, 1985

[51] Int. Cl.$^4$ ............................................. C07F 7/08
[52] U.S. Cl. .................................................. 556/478
[58] Field of Search ....................................... 556/478

[56] References Cited

U.S. PATENT DOCUMENTS 3,103,526  9/1963  Jenkner ..................... 556/478 X
3,927,058 12/1975  Libbey ........................ 556/478
3,927,059 12/1975  Libbey et al. ............... 556/478

FOREIGN PATENT DOCUMENTS 825987 12/1959 United Kingdom ........ 556/478 UX

*Primary Examiner*—Paul F. Shaver
*Attorney, Agent, or Firm*—Roylance, Abrams, Berdo & Goodman

[57] ABSTRACT

A process for the production of tetra- and trialkylsilanes which comprises reacting
  (A) an alkylchlorosilane having the formula $$R_xSiCl_{(4-x)}$$

wherein R is an alkyl radical containing from one to three carbon atoms per molecule and x is an integer from 0 to 3, with
  (B) a trialkylaluminum compound having the formula $$\begin{array}{c} R_2 \\ | \\ R_1-Al \\ | \\ R_3 \end{array}$$

wherein $R_1$, $R_2$ and $R_3$ are the same or different and represent alkyl radicals containing from 6 to 20 carbon atoms per molecule, in a reaction zone, said reaction being conducted under hydrosilylation conditions. Selectivity to tetra- or trialkylsilanes, respectively, is controlled by the addition of particular alkaline metal salts to the reaction zone.

14 Claims, No Drawings

SILAHYDROCARBONS FROM ALKYLCHLOROSILANES

FIELD OF THE INVENTION

The present invention relates to the production of alkylsilane synthetic fluids, also known as silahydrocarbons. More particularly, this invention relates to the production of tetra- and trialkyl substituted silanes by reacting trialkylaluminum compounds with chloro- or alkylchlorosilanes.

BACKGROUND INFORMATION

Various synthetic fluids, including synthetic hydrocarbons and silahydrocarbons, have been developed which are useful in the formulation of hydraulic fluids and lubricants which are stable at high temperatures. Tetraalkyl substituted silanes have been proposed for use in the formulation of hydraulic fluids and lubricants since they possess excellent viscosities over a wide temperature range and low pour points in addition to excellent thermal stability.

Various methods for the synthesis of tetraalkyl substituted silanes possessing the desired properties involving the addition of a Grignard reagent or alkyllithium compounds to alkyltrichlorosilanes have been reported in U.S. Pat. No. 4,367,343 to Tamborski et al; Rosenberg et al, *J. Org. Chem.*, 1960, Vol. 25, pp. 243-248; pp. 142-145. The preparation of ethyl-substituted silanes from triethylaluminum and chloro- or alkylchlorosilanes is described in British Pat. No. 825,987 to Kali-Chemie Aktiengesellschaft. However, such lower alkyl-substituted silanes are unsuitable for use in the formulation of hydraulic fluids and lubricants which are stable at high temperatures.

SUMMARY OF THE INVENTION

It has now been found that tetraalkylsubstituted silane compounds which are useful in the formulation of hydraulic fluids and lubricants stable at high temperatures can be produced by heating a mixture of an alkylchlorosilane and a trialkyl aluminum compound. More specifically, the process of the present invention comprises reacting (A) an alkylchlorosilane having the formula $$R_xSiCl_{(4-x)}$$

wherein R is an alkyl radical containing from one to twenty carbon atoms per molecule and x is an integer from 0 to 3, with (B) a trialkylaluminum compound having the formula

wherein $R_1$, $R_2$ and $R_3$ are the same or different and represent alkyl radicals containing from six to twenty carbon atoms per molecule, in a reaction zone, the reaction being conducted under alkylation conditions.

The desired tetraalkylsilane product has the general formula

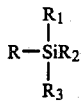

wherein R, $R_1$, $R_2$ and $R_3$ are as defined above.

In accordance with a preferred embodiment of the present invention, it has been found that the selectivity of the alkylation reaction of the present invention can be controlled to favor the production of tetraalkylsilane or trialkylsilane product, respectively, depending upon the addition of a particular alkaline metal salt. For example, addition of a sodium halide, such as sodium chloride favors production of the tetraalkylsilane over the corresponding trialkylsilane product, such as a trialkylsilane having the formula

wherein R, $R_1$ and $R_3$ are defined above.

Additionally, it has been found that if a lithium salt, such as a lithium halide, for example, lithium chloride, in particular, is added to the alkylation zone, such addition favors the production of the tetraalkylsilane and results in virtually no trialkylsilane being produced.

In accordance with another embodiment of the present invention, if the alkali metal salt added is a potassium salt or rubidium salt, such as a potassium or rubidium halide, particularly potassium chloride or rubidium chloride, this results in the production of a major amount of the trialkylsilane as compared with a minor amount of the tetraalkylsilane.

In those embodiments of the present invention in which an alkali metal salt is utilized to favor the production of a trialkylsilane product, the trialkylsilane may be converted in a separate step to form tetraalkylsilane by any suitable process. A particularly preferred means of converting the trialkylsilanes of the present invention to tetraalkylsilanes suitable for use in the formulation of hydraulic fluids and lubricants stable at high temperatures is described in U.S. patent application Ser. No. 677,047, filed on Nov. 30, 1984 in the name of Anatoli Onopchenko and Edward T. Sabourin entitled "Tetraalkylsilane Synthetic Fluids", the disclosure of which is hereby incorporated by reference.

DESCRIPTION OF THE PREFERRED EMBODIMENTS

As previously indicated, the process of the present invention comprises a reaction involving an alkylchlorosilane having the formula $$R_xSiCl_{(4-x)}$$

wherein R is an alkyl radical containing from one to twenty carbon atoms per molecule and x is an integer from 0 to 3.

Suitable alkylchlorosilanes include tetrachlorosilane, dimethyldichlorosilane, diethyldichlorosilane, dipropyldichlorosilane, methyl ethyldichlorosilane, methyl propyldichlorosilane, ethylpropyldichlorosilane, trimethylchlorosilane, triethylchlorosilane, tripropylchlorosilane, butyltrichlorosilane, hexyltrichlorosilane, octyltrichlorosilane, decyltrichlorosilane, dodecyltrichlorosilane, tetradecyltrichlorosilane, hexadecyltrichlorosilane, octadecyltrichlorosilane, eicosyltrichlorosilane, methyl hexyldichlorosilane, methyl octyldichlorosilane, methyl decyldichlorosilane, methyl dodecyltrichlorosilane, methyl hexadecyldichlorosilane, methyl octadecyldichlorosilane.

Preferably, the alkylchlorosilane used in the process of the present invention is a monoalkyl trichlorosilane having the formula $$RSiCl_3$$

wherein R is an alkyl radical containing from one to three carbon atoms. Preferred monoalkyl trichlorosilanes include, for example, methyltrichlorosilane, ethyltrichlorosilane and n-propyltrichlorosilane.

The alkylchlorosilane is reacted with a trialkylaluminum compound having the formula $$R_1-Al\begin{matrix}R_2\\ \\R_3\end{matrix}$$

wherein $R_1$, $R_2$ and $R_3$ are the same or different and represent alkyl radicals having from six to twenty carbon atoms per molecule, preferably eight to fourteen carbon atoms per molecule.

Examples of the preferred trialkylaluminums include tri-n-hexylaluminum, tri-n-octylaluminum, tri-n-decylaluminum, tri-n-dodecylaluminum, di-n-octyl-n-decylaluminum, di-n-octyl-n-dodecylaluminum, di-n-octyl-n-hexylaluminum, n-octyl-di-n-decylaluminum, n-octyl-n-decyl-n-dodecylaluminum and the like and mixtures thereof.

The reaction is carried out at a temperature from 150° to 300° C., preferably from 160° to 220° C. in an inert atmosphere, such as, nitrogen or the noble gases. The pressure may be the autogenous pressure attained by heating the reactants in a closed vessel, or preferably an elevated pressure of from about 1 to about 100 atmospheres under an inert gas such that the more volatile components are kept predominantly in the liquid phase. The reaction time is from 0.5 hours to 24 hours, preferably from one to 6 hours.

The particular alkaline metal salt utilized will control selectivity to a tetra- or a trialkylsilane product. The alkali metal salt is preferably an alkali metal halide, with an alkali metal chloride being especially preferred.

As previously indicated, the use of a sodium salt favors the production of the tetraalkylsilane over the trialkylsilane. Suitable amounts of the alkali metal salt include from about 0.4 to about 10, preferably from about 0.5 to about 2 molar equivalents of the salt relative to the amount of the aluminum compound. It has been found that the addition of sodium chloride in an amount which is 0.5 molar equivalent or more relative to the amount of aluminum compound is beneficial in reducing competing reactions which result in disproportionation products of the type $$RSiR_1\begin{matrix}R\\ \\R_2\end{matrix} \text{ and } R_3SiR_1\begin{matrix}R_3\\ \\R_2\end{matrix}$$

wherein R, $R_1$, $R_2$ and $R_3$ are defined as above.

It was particularly surprising to find that only one-half equivalent of sodium chloride is required to suppress such side reaction, and as hereinafter demonstrated, little or no change in product distribution is observed by using more than that amount.

EXAMPLES 1–5

Tests were run in a thick walled glass reactor equipped with a magnetic stirrer, a heating mantle controlled by a West temperature controller, and thermocouple. The vessel was attached to a nitrogen inlet-outlet system with via Fisher-Porter Glass-Pipe Compression fittings. A similar compression fitting attached to a side arm connected to a wide bore valve equipped with a rubber septum to allow the addition of the air sensitive reagents via syringe.

The reaction vessel was charged with 85 millimoles of sodium chloride and attached to a nitrogen supply system. This was purged from the system by pressuring to 30 psig and venting, ten times. Tri-n-octylaluminum in the amount of 85 millimoles was added via syringe followed by the addition of 70 millimoles of methyltrichlorosilane. The mixture was stirred and heated to 200° C. After 3 hours, the vessel was cooled to room temperature and 50 milliliters of heptane were added. The vessel was opened and the contents were flushed out with more heptane. Sufficient methanol was added cautiously to quench any remaining aluminum alkyl or chlorosilanes and to dissolve the aluminum chloride complex. Water was then added to facilitate separation of the heptane layer. The heptane layer was dried over a magnesium sulfate, filtered and stripped. Analysis by gas chromatography on a 12.5 meter fused silica OV-101 column showed a yield of 61.3 mole percent methyltri-n-octylsilane along with 3.4 mole percent dimethyldi-n-octylsilane, 3.0 mole percent tetra-n-octylsilane and 2.4 mole percent methyldi-n-octylsilane based on methyltrichlorosilane.

The foregoing procedure was repeated using varying amounts of sodium chloride. The tests results are set forth in Table I below:

TABLE I

| | Reactants, mmoles | | | | | Yield, Mole %[c,d] | | | | |
|---|---|---|---|---|---|---|---|---|---|---|
| Example | TNOA[a] | MTCS[b] | NaCl | Temp. °C. | Time, h | MO$_3$Si | O$_4$Si | MO$_2$SiH | M$_3$OSi | M$_2$O$_2$Si |
| 1 | 85 | 70 | 85 | 200 | 3 | 61.3 | 3.0 | 2.4 | — | 3.4 |
| 2 | 85 | 68 | 85 | 210 | 1 | 58.5 | 0.6 | 0.7 | — | 3.2 |
| 3 | 85 | 71 | 43 | 210 | 5.5 | 63.4 | 3.9 | — | — | 5.6 |
| 4 | 85 | 70 | 21 | 220 | 2 | 33.1 | 21.3 | — | 2.6 | 13.0 |
| 5 | 85 | 70 | 0 | 220 | 6 | 26.1 | 21.7 | — | 3.4 | 8.7 |

[a]TNOA = tri-n-octylaluminum
[b]MTCS = methyltrichlorosilane
[c]M = methyl; O = octyl; H = hydrogen. Yield based on MTCS limiting reagent.
[d]Based on MTCS as limiting reagent.

The results set forth in Table I show that little advantage is obtained in the production of methyl-tri-n-octylsilane by using more than 0.5 equivalent of sodium chloride relative to the aluminum compound, tri-n-octylaluminum. The omission of sodium chloride results in a yleld of only 26.1 mole percent, while the highest yield, 63.4 mole percent, is achieved using approximately an 0.5 molar equivalent of sodium chloride relative to the alkylaluminum (TNOA). When larger quantities of sodium chloride were used up to one molar equivalent, as in Examples 1 and 2, the yield of the tetraalkylsilane (61.3 mole percent and 58.5 mole percent, respectively) did not exceed the yield when only 0.5 molar equivalent of sodium chloride was used.

Examples 1–3, illustrative of the current invention, show relatively little difference in selectivity in the time range 1–5.5 hours. Example 4, outside the desired NaCl limits, but of intermediate time (2 hours) already shows a dramatic loss of selectivity. Example 5 shows that extending the time in a non-selective run does not have a beneficial effect.

EXAMPLES 6–14

The procedure of Examples 1–5 were repeated, but at various temperatures from 160° C. to 230° C. The results are set forth in Table II, below:

TABLE II[a]

| | Reactants, mmoles | | | | | Yield, mole % | | | | |
|---|---|---|---|---|---|---|---|---|---|---|
| Example | TNOA | MTCS | NaCl | Temp. °C. | Time, h | M$_3$OSi | M$_2$O$_2$Si | MO$_3$Si | O$_4$Si | MO$_2$SiH |
| 6 | 100 | 99 | 100 | 160 | 7 | 0.5 | 1.9 | 59.0 | 4.0 | 1.2 |
| 7 | 100 | 86 | 100 | 170 | 5 | — | 1.9 | 70.0 | 8.3 | 1.3 |
| 8 | 108 | 90 | 100 | 180 | 4 | 0.9 | 3.8 | 63.2 | 2.1 | 2.4 |
| 9 | 108 | 94 | 115 | 180 | 3 | — | 2.4 | 65.8 | 1.8 | 3.0 |
| 10 | 105 | 88 | 100 | 190 | 3 | 0.2 | 2.7 | 72.1 | 2.6 | 1.8 |
| 11 | 100 | 68 | 100 | 190 | 3 | — | 2.5 | 69.9 | 3.8 | 1.5 |
| 12 | 100 | 82 | 100 | 190 | 3 | — | 2.3 | 72.3 | 4.9 | 1.7 |
| 1 | 85 | 70 | 85 | 200 | 3 | — | 3.4 | 61.3 | 3.0 | 2.4 |
| 13 | 108 | 95 | 100 | 200 | 3 | 0.3 | 3.2 | 68.1 | 2.7 | 1.7 |
| 14 | 101 | 98 | 101 | 230 | 5.5 | — | 6.1 | 53.7 | 4.3 | 1.7 |

[a]See Table I for explanation of symbols.

As seen in Table II, it is apparent that at the lower temperatures, longer reaction times are required to attain the same yield. Higher temperatures and longer reaction time contribute to a moderate increase in the disproportionation products. Small variations in the ratio of aluminum to alkylchlorosilane at a given temperature have little effect on yield as long as the aluminum is in excess. The tests of Table II also demonstrate that small variations in temperature did not cause the loss in selectivity shown in Table I.

EXAMPLE 15

Utilizing the apparatus of Examples 1–5, 100 millimoles of potassium chloride, 100 millimoles of tri-n-octylaluminum, and 98 millimoles of methyltrichlorosilane were reacted at 180° C. for 4 hours. The analyses utilized in Examples 1–5 revealed that only 8.3% mole percent methyltrioctylsilane was produced as compared with 63–66 mole percent methyltrioctylsilane that was produced using comparable conditions but adding sodium chloride (compare Examples 8 and 9 from Table II). The major product, methyldioctylsilane was produced in a 47.2 weight percent yield. Product was identified by characteristic infrared Si—H found at 2100 cm$^{-1}$; independent synthesis by reaction of methyldichlorosilane with two equivalents of n-octyl-magnesium bromide; and conversion under hydrosilylation conditions with octene to methyltrioctylsilane. This clearly demonstrates a different mode of action for sodium chloride versus potassium chloride.

EXAMPLE 16

Utilizing the apparatus of Examples 1–5, 50 millimoles of sodium chloride, 100 millimoles of tri-n-octylaluminum, and 73 millimoles of tetrachlorosilane were reacted for 4 hours at 180° C. The analysis utilized in Examples 1–5 revealed that 62.9 mole percent tetraoctylsilane and 6.8 mole percent trioctylchlorosilane were produced based on tetrachlorosilane as the limiting reagent.

What is claimed is:

1. A process for the production of tetra- and trialkylsilanes which comprises reacting (A) an alkylchlorosilane having the formula $$R_xSiCl_{(4-x)}$$

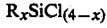

wherein R is an alkyl radical containing from one to three carbon atoms per molecule and x is an integer from 0 to 3, with (B) a coreactant consisting essentially of a trialkylaluminum compound having the formula

wherein R$_1$, R$_2$ and R$_3$ are the same or different and represent alkyl radicals containing from 6 to 20 carbon atoms per molecule, in a reaction zone, said reaction being conducted under hydrosilylation conditions.

2. The process of claim 1 wherein the relative amounts of tetra- and trialkylsilanes produced are controlled by adding an alkali metal salt to said reaction zone.

3. The process of claim 2 wherein a sodium salt is added to the reaction zone to maximize the amount of tetraalkylsilane produced.

4. The process of claim 3 wherein said sodium used is about 0.5 molar equivalent relative to said trialkylaluminum compound.

5. The process of claim 2 wherein said alkali metal salt is a potassium salt, and the addition of said potassium salt maximizes the amount of trialkylsilane produced.

6. The process of claim 2 wherein a lithium salt is added to said reaction zone to maximize the amount of tetraalkylsilane produced.

7. The process of claim 6 wherein said lithium salt is lithium chloride.

8. The process of claim 2 wherein a rubidium salt is added to the reaction zone and said salt causes the formation of a major amount of trialkylsilane as compared with tetraalkylsilane.

9. The process of claim 1 wherein said alkylchlorosilane is methyl trichlorosilane, ethyltrichlorosilane or n-propyltrichlorosilane.

10. The process of claim 1 wherein said trialkylaluminum compound is tri-n-hexylaluminum, tri-n-octylaluminum or tri-n-decylaluminum.

11. The process of claim 1 wherein said reaction zone is maintained at a temperature in the range of from about 150° to about 300° C.

12. The process of claim 11 wherein said reaction zone is maintained at a temperature of from about 160° to about 220° C.

13. The process of claim 1 wherein $R_1$, $R_2$, and $R_3$ represent alkyl radicals containing from 8 to 14 carbon atoms.

14. The process of claim 3 wherein a major amount of tetraalkylsilane is formed as compared with the amount of trialkylsilane formed.

* * * * *